United States Patent [19]

Sakakibara et al.

[11] 4,358,621

[45] Nov. 9, 1982

[54] PROCESS FOR PRODUCING ALDEHYDES

[75] Inventors: Tadamori Sakakibara; Yoshihisa Matsushima, both of Ooi; Katsumi Kaneko, Tokyo, all of Japan

[73] Assignee: Toa Nenryo Kogyo Kabushiki Kaisha, Tokyo, Japan

[21] Appl. No.: 266,646

[22] Filed: May 26, 1981

[30] Foreign Application Priority Data

May 28, 1980 [JP] Japan .................................. 55-70064

[51] Int. Cl.$^3$ .............................................. C07C 45/50
[52] U.S. Cl. .................................. 568/454; 568/452; 252/431 P; 260/429.7
[58] Field of Search ............... 568/454, 452, 882, 909; 260/429.7; 252/431 P

[56] References Cited

U.S. PATENT DOCUMENTS

| | | | |
|---|---|---|---|
| 3,239,571 | 3/1966 | Slaugh et al. | 568/454 |
| 3,876,672 | 4/1975 | Mrowca | 568/454 |
| 3,981,925 | 9/1976 | Schwager et al. | 568/454 |
| 3,996,293 | 12/1976 | Knifton et al. | 568/454 |
| 4,013,584 | 3/1977 | Knifton | 568/454 |
| 4,101,564 | 7/1978 | Poist | 568/454 |
| 4,101,565 | 7/1978 | Poist | 568/454 |
| 4,198,352 | 4/1980 | Kim et al. | 568/454 |
| 4,229,381 | 10/1980 | Ogata et al. | 568/454 |
| 4,283,563 | 8/1981 | Kawabata et al. | 568/454 |
| 4,299,985 | 11/1980 | Knifton et al. | 568/454 |

FOREIGN PATENT DOCUMENTS

| | | | |
|---|---|---|---|
| 55-73692 | 12/1980 | Japan | 568/454 |
| 1368433 | 9/1974 | United Kingdom | 568/454 |
| 1391395 | 4/1975 | United Kingdom | 568/454 |

OTHER PUBLICATIONS

J. Am. Chem. Soc., vol. 97, p. 3553 (1975) by C. Y. Hsu and M. Orchin.
Derwent Abstract-Japanese Pat. Appln. 73692-published Dec. 22, 1980.
J. Chem. Soc. (A), pp. 1542-1546 (1970), by P. Chini et al.
Inorg. Chem., vol. 4, pp. 16-18 (1965), by J. C. Bailar, Jr. et al.
J. Org. Chem., vol. 34, pp. 327-330 (1969) by R. L. Pruett et al.
J. Chem. Soc. A, pp. 3133-3142 (1968) by D. Evans et al.
J. Organo, Metal. Chem., vol. 13, pp. 469-477 (1968) by Slaugh et al.* *
J. Chem. Soc. (A), 1970, pp. 2594-2598, Cardin et al.
J. Chem. Soc. Dalton, pp. 767-776 (1976) by C. Eaborn.
J. Inorg. Nucl. Chem., vol. 29, pp. 367-373 (1967) by M. C. Baird.
J. of Catalysis, vol. 45, pp. 256-267 (1976) by Schwager et al.
J. Amer. Chem. Soc., vol. 797, p. 3553 (1975).
J. Organometal. Chem., vol. 213, pp. 503-512 (1981).
Mitsui Pet. Japanese Pat. Abstract 5 3065 810 (12-6-78), 52396A29 E19.
Agency of Ind. Sci. Tech. "Japanese Patent Abstract J 5 5100-331 (7-31-80), 65044 C/37E17.

*Primary Examiner*—Werren B. Lone
*Attorney, Agent, or Firm*—Robert J. North

[57] ABSTRACT

Described is an olefin hydroformylation process for producing aldehydes utilizing a Pt Group IV-A organometallic catalyst mixture such as $(PPh_3)_2PtPh\text{-}SnPh_2Cl/SnCl_2$. High yields of aldehydes are produced in high selectivity for the normal isomer, especially when using propylene as the olefin.

11 Claims, No Drawings

PROCESS FOR PRODUCING ALDEHYDES

BACKGROUND OF THE INVENTION

This invention relates to the oxo process for producing aldehydes by reacting an olefin with carbon monoxide and hydrogen in the presence of a platinum-Group VI-A catalyst mixture.

A representative example of the oxo process which is industrially employed is the production of n-butyraldehyde from propylene as the starting material, and the obtained n-butyraldehyde is consumed in large amounts as the intermediate for plasticizers for vinyl chloride. However, the conventional oxo process employing a cobalt catalyst also produces a considerable amount of isobutyraldehyde as a byproduct. Isobutyraldehyde has a low utilization value and thus its formation is not desired.

In addition, for the production of higher alcohols for detergents from higher olefins, it is desired to selectively produce linear aldehydes.

Thus, the important problem in the industrial oxo process is to increase the yield of a linear aldehyde and at the same time to inhibit formation of a branched aldehyde.

Newer and more efficient catalysts to achieve these ends are constantly being searched for.

SUMMARY OF THE INVENTION

It has been discovered that utilizing certain platinum organometallic catalyst mixtures comprised of a platinum (II) organometallic compound containing a Group IV-A metal and a dihalide of Ge, Sn or Pb, in the oxo process, linear aldehydes can be obtained at a high reaction rate and in high selectivity.

Accordingly, this invention provides a process for producing aldehydes which comprises reacting an olefin with a mixture of hydrogen and carbon monoxide, in a molar ratio of about 1:20 to 20:1, at a temperature of about 15°–150° C., and a pressure of about 0.1-30 MPa, in the presence of a catalyst mixture comprising:

(a) a platinum (II) organometallic compound of the following general formula:

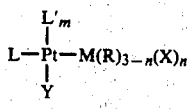

wherein M represents Si, Ge, Sn or Pb; L represents an unidentate or bidentate liquid containing P, As or Sb; L' represents a coordination compound; Y represents an alkyl group, an aryl group, an alkoxy group, an aryloxy group, or hydrogen; R independently represents an alkyl group, an aryl group, an alkoxy group or an aryloxy group; X independently represents halogen or hydrogen; n represents an integer of 0, 1 or 2; and m is 1 when L is an unidentate ligand or 0 when L is a bidentate ligand; and (b) a dihalide of Ge, Sn or Pb.

DETAILED DESCRIPTION OF THE INVENTION AND PREFERRED EMBODIMENTS

The oxo process which employs the catalyst system according to this invention can produce linear aldehydes in high selectivity and high yield and especially in the case of propylene, n-butyraldehyde can be obtained in very high selectivity.

The platinum (II) organometallic compound is, as mentioned above, a complex compound of the following general formula:

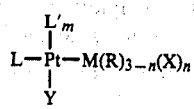

In the above, L is an unidentate or bidentate ligand contaning phosphorus, arsenic or antimony, specific examples of which include unidentate ligand of the general formula: $Z(R')(R'')(R''')$ wherein Z represents P, As or Sb and R', R'' and R''' independently represent an alkyl group, an alkoxy group, an aryl group or an aryloxy group, and R', R'' and R''' may be the same or different; bidentate ligands of the general formula:

wherein Z represents P, As or Sb, D represents a methylene group or its substituted derivative or an oxygen atom, A represents an alkylene group of 1–6 carbon atoms, an arylene group or an aralkylene group, and R and R' independently represent an alkyl group, an aryl group, an alkoxy group or an aryloxy group, and R and R' may be the same or different; and the like. Specific examples of these compounds are given below.

In this invention, it is intended that the term "alkyl group" includes a cycloalkyl group and the terms "aralkyl group" and "alkoxy group" include cycloalkoxy and aralkyloxy group. The phenyl group is abbreviated as Ph.

In the unidentate ligands, representative examples of the phosphorus compounds of the above general formula include tertiary phosphine compounds such as trimethylphosphine, triethylphosphine, tripropylphosphine, tributylphosphine, tricyclohexylphosphine, triphenylphosphine, tritolylphosphine, trichlorophenylphosphine, dimorpholinophenylphosphine etc.; tertiary phosphite compounds such as trimethyl phosphite, triethyl phosphite, tripropyl phosphite, tributyl phosphite, tricyclohexyl phosphite, triphenyl phosphite, trichlorophenyl phosphite etc.; tertiary phosphinite compounds such as ethyl diethylphosphinite, ethyl dipropylphosphinite, phenyl diphenylphosphinite etc.; tertiary phosphonite compounds such as dimethyl phenylphosphonite, diethyl butylphosphonite diphenyl phenylphosphonite etc. and the like.

Representative Examples of arsenic compounds applicable as unidentate ligands in the described catalyst mixture herein include tertiary arsine compounds such as trimethylarsine, triethylarsine, tripropylarsine, tributylarsine, tricyclohexylarsine, triphenylarsine, tritolylarsine, trichlorophenylarsine etc.; arsenious acid esters such as trimethyl arsenite, triethyl arsenit, tri-n-propyl arsenite, triisopropyl arsenite, tri-n-butyl arsenite, tri-sec-butyl arsenite, tri-tert-butyl arsenite, triphenyl arsenite, tritolyl arsenite, trichlorophenyl arsenite, and the like.

Representative examples of the antimony compounds include tertiary stibine compounds such as trimethylstibine, triethylstibine, tri-n-propylstibine, triisopropylstibine, tri-n-butylstibine, tri-sec-butylstibine, tri-tert-butylstibine, triphenylstibine, tritolylstibine, trichlorophenylstibine etc., and the like. Among these ligands, it is peferred to employ at least one ligand selected from the group consisting of the tertiary phosphine compounds, tertiary phosphite compound, tertiary phosphinate compounds, tertiary phosphonite compounds and tertiary arsine compounds of the above general formula, and it is particularly preferred to employ the tertiary phosphine compounds or the tertiary arsine compounds, especially the use of triphenylphosphine and triphenylarsine being preferred.

In the bidentate ligands of the above general formula to be used in this invention, the groups represented by R, R', A and C respectively, may be further substituted by other substituent groups which do not interfere in the reaction. Representative examples of the aforementioned preferred bidentate ligands in this invention include 1,2-bis(diphenylphosphino)ethane Ph$_2$PCH$_2$CH$_2$PPh$_2$, 1,3-bis (diphenylphosphino)propane Ph$_2$P(CH$_2$)$_3$PPh$_2$, 1,4-bis(diphenylphosphine)butane Ph$_2$P(CH$_2$)$_4$PPh$_2$, 1,5-bis(diphenylphosphino)pentane Ph$_2$P(CH$_2$)$_5$PPh$_2$, 1,2-bis(diphenylphosphinomethyl)cyclobutane (DIBDPMCB)

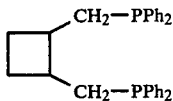

2,3-o-isopropylidene-2,3-dihydroxy-1,4-bis(diphenylphosphinomethyl)butane (DIOP)

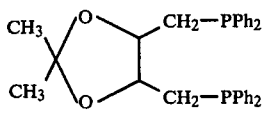

1,2-bis(diphenylphosphinoxy)cyclopentane (BDPCP)

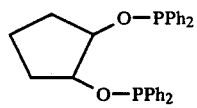

1,2-bis(diphenylphosphinomethyl)cyclopentane (BDPMCP)

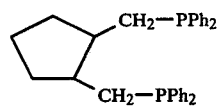

1,2-bis(diphenylphosphinomethyl)cyclohexane (BDPMCH)

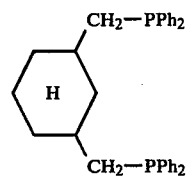

1,3-bis(diphenylphosphinoxy)cyclohexane

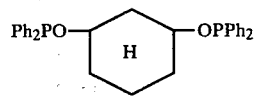

1,2-bis(diphenylphosphinomethyl)benzene

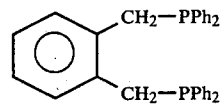

1,2-bis(diphenylphosphinoxy)benzene

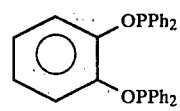

1,8-bis(diphenylphosphinomethyl)naphthalene

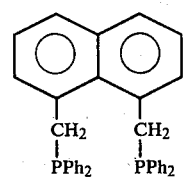

1,2-bis(diphenylarsino)cyclobutane, 2,3-o-isopropylidene-2,3-dihydroxy-1,4-bis(diphenylarsino)butane, as well as their arsenic and antimony analogs.

Especially preferred bidentate ligands in this invention are DIBDPMCB, BDPMCH, BDPCP AND BDPMCP.

The coordination compounds represented by L' include, in addition to the unidentate ligands described above containing phosphorus, arsenic and antimony, illustrated by the examples for the afore-mentioned ligands represented by L, carbon monoxide, as well as ligands containing nitrogen, oxygen and sulfur. Representative examples thereof include carbon monoxide (CO), nitrile compounds (RCN), isonitrile compounds (RNC), amine compounds (R$_3$N), cyano (CN), nitrosyl (NO), ether compounds (R$_2$O), alcohol compounds (ROH), thioether compounds (R$_2$S) and the like. Further, among these ligands, more specific examples of the amine compounds include aliphatic amines such as methylamine, ethylamine, propylamine, butylamine, cyclohexylamine, dimethylamine, diethylamine, dipropylamine, dicyclohexylamine, trimethylamine, triethylamine, tributylamine, piperidine, piperazine, ethylenediamine, diethylenetriamine, and the like; aromatic amines such as pyridine, picoline, lutidine, aniline, methylaniline, dimethylaniline, quinoline, acridine, phenanthroline, dipyridyl, and the like.

Y represents an alkyl group, an aryl group, an alkoxy group, an aryloxy group, or hydrogen. More specifically, the alkyl group includes methyl, ethyl, n-butyl, i-butyl, pentyl, hexyl, cyclohexyl, methylcyclohexyl etc.; the aryl group includes phenyl, tolyl, benzyl, phenethyl etc.; the alkoxy group includes methoxy, ethoxy, propoxy, butoxy, pentoxy, cyclohexyloxy; and the aryloxy group includes phenoxy, methylphenoxy and the like.

R represents an alkyl group, an aryl group, an alkoxy group or an aryloxy group, and specific examples thereof include those illustrated by the above-described Y.

X is halogen or hydrogen, and specific examples of the halogen are fluorine, chlorine, bromine and iodine.

n represents an integer of 0, 1 or 2. m is 1 when L' is an unidentate ligand, or 0 when L' is a bidentate ligand, and the R groups independently may be the same or different.

Especially preferred specific examples, among the platinum (II) compounds to be used in this invention are given below, but this invention shall not be restricted to these specific examples.

(1) $(PPh_3)_2(Ph)Pt-Sn(Ph)_2Cl$
(2) $(PPh_3)_2(Ph)Pt-Sn(Ph)_3$
(3) $(PPh_3)_2(Ph)Pt-Sn(CH_3)(Ph)Cl$
(4) $(PPh_3)_2(Ph)Pt-Sn(CH_3)_2Cl$
(5) $(PPh_3)_2(CH_3)Pt-Sn(CH_3)_2Cl$
(6) $(PPh_3)_2(CH_3-C_6H_4)Pt-Sn(CH_3-C_6H_4)_2Cl$
(7) $(PPh_3)_2(Ph)Pt-Sn(Ph)_2Br$
(8) $(PPh_3)_2(Ph)Pt-Sn(Ph)_2I$

The platinum (0) compound used in this invention is now more particularly described.

L is the platinum (0) compound of the above general formula: $Pt(L)(L')_{n'}$ to be used for the synthesis of the platinum (II) compound of this invention or as the catalyst starting material represents an unidentate or bidentate ligand containing phosphorus, arsenic or antimony, and L' represents a coordination compound. Specific examples of L include the same compounds as those illustrated by the platinum (II) compounds of the above general formula: $(L)(L')_mPt-M(R)_{3-n}(X)_n$. Specific examples of L' include, in addition to the coordination compounds illustrated by the above-described platinum (II) compounds of the formula: $(L)(L')_mPt-M(R)_{3-n}(X)_n$, olefin compounds, acetylene compounds, diene compounds, diketone compounds, and the like. More specifically, they are ethylene ($CH_2=CH_2$), diphenylacetylene ($PhC≡PhC$), dibenzylidene acetone

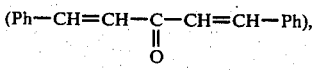

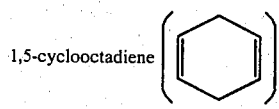  1,5-cyclooctadiene

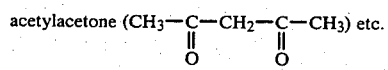 acetylacetone ($CH_3-C-CH_2-C-CH_3$) etc.

Among the platinum (0) compounds in this invention, especially preferred compounds are shown below, but this invention shall not be restricted to these compounds.

(1) $Pt(PPh_3)_4$: tetrakis(triphenylphosphine)platinum (0)
(2) $Pt(PPh_3)_3$: tris(triphenylphosphine)platinum (0)
(3) $Pt(CO)_2(PPh_3)_2$: dicarbonylbis(triphenylphosphine)platinum (0)
(4) $Pt(CO)(PPh_3)_3$: carbonyltris(triphenylphosphine)platinum (0)
(5) $Pt(CH_2=CH_2)(PPh_3)_2$: ($\eta$-ethylene)bis(triphenylphosphine)platinum (0)
(6) $Pt(PhC≡CPh)(PPh_3)_2$: (diphenylacetylene)bis(trisphenylphosphine)platinum (0)

(7) $Pt(PhCH=CH-C(=O)-CH=CHPh)(PPh_3)_2$: (dibenzylideneacetone)bis-(triphenylphosphine) platinum (0)

M in the Group IV-B organometallic compound of the general formula: $YM(R)_{3-n}(X)_n$ to be used for the synthesis of the platinum (II) compound of this invention or as the catalyst starting material represents Si, Ge, Sn or Pb; Y represents an alkyl group, an aryl group, an alkoxy group, an aryloxy group, or hydrogen; X represents a halogen or hydrogen, and R represents an alkyl group, an aryl group, an alkoxy group or an aryloxy group.

Among the Group IV-A organometallic compounds in this invention, especially preferred compounds are shown below, but this invention shall not be restricted to these compounds.

(1) $SnPh_4$: tetraphenyltin
(2) $Sn(n-C_4H_9)_4$: tetra-n-butyltin
(3) $Sn(CH_3)_4$: tetramethyltin
(4) $Sn(Ph)_3Cl$: triphenyltin chloride
(5) $Sn(C_2H_5)_3Cl$: triethyltin chloride
(6) $Sn(CH_3)_3Cl$: trimethyltin chloride
(7) $Sn(C_6H_5-CH_3)_2Cl_2$: dibenzyltin dichloride
(8) $Sn(CH_3)_2Cl_2$: dimethyltin dichloride
(9) $Sn(n-C_4H_9)_2I_2$: di-n-butyltin diiodide
(10) $Sn(n-C_4H_9)Cl_3$: n-butyltin trichloride
(11) $Sn(Ph)_3H$: triphenyltin hydride
(12) $Sn(n-C_4H_9)_3H$: tri-n-butyltin hydride
(13) $Sn(C_2H_5)_3H$: triethyltin hydride
(14) $Sn(n-C_4H_9)_2H_2$: di-n-butyltin dihydride
(15) $Sn(n-C_4H_9)H_3$: n-butyltin trihydride
(16) $Ge(Ph)_4$: tetraphenylgermane
(17) $Ge(Ph)_3Cl$: triphenylgermanium chloride The platinum (II) compounds of this invention may, as described above, be easily synthesized by mixing solutions of the platinum (0) compound and the aforementioned Group IV-A organometallic compound.

These platinum (II) compounds may be easily obtained by the oxidative addition reaction of the aforementioned platinum (0) compound of the general formula: $Pt(L)(L')_n$, and the organometallic compound of the general formula: $YM(R)_{3-n}(X)_n$, as follows:

$Pt(L)(L')_{n'} + YM(R)_{3-n}(X)_n \rightarrow Pt(L)(L')(Y)-M(R)_{3-n}(X)_n + (L')_{n'-1}$ Where (L')'s of n' in number are different and represented by $L^1$ and $L^2$, or $L^1$, $L^2$ and $L^3$, the platinum (II) compound may be obtained by either of the following reaction formulae:

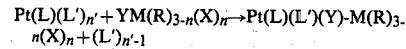

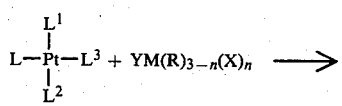

or

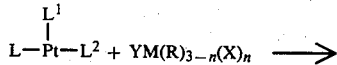

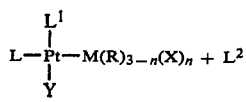

More specifically, for example (PPh$_3$)$_2$(Ph)Pt-Sn(Ph)$_2$Cl may be obtained as white crystals by the method described in C. Eaborn et al., J. Chem. Soc. Dalton 767-776 (1976), hereby incorporated by reference, by mixing and stirring a solution of ($\eta$-ethylene)-bis(triphenylphosphine)platinum (0) [(PPh$_3$)$_2$Pt(C$_2$H$_4$)] in benzene and a solution of triphenyltin chloride [Sn(Ph)$_3$Cl] in benzene at about 50° C. for an hour and subsequently allowing the reaction mixture to stand, i.e.,

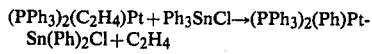

In a similar manner, (PPh$_3$)$_2$(Ph)Pt-SnPh$_3$ may be synthesized from (PPh$_3$)$_2$Pt(C$_2$H$_4$) and (Ph)$_4$Sn.

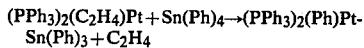

Therefore, while the platinum (II) compounds of this invention may be synthesized separately and used, they can also be synthesized in situ in the oxo reaction system directly from the platinum (0) compound and the aforementioned Group IV-A organometallic compound.

In addition, the platinum (II) organometallic compounds of this invention may also be synthesized by other methods than those described above, for example, by the following methods, herein incorporated by reference:

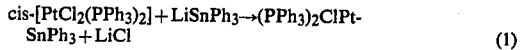

Literature: M. C. Baird, J. Inorg. Nuclear Chem., 1967, 29, 367.

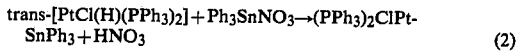

Literature: Same as for (1) above.

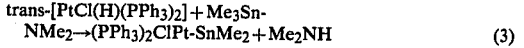

Literature: M. F. Lappert et al, J. Chem. Soc. (A) 1970, 2594.

The dihalide of Ge, Sn or Pb include the following representative examples:
Sn: SnCl$_2$, SnBr$_2$, SnI$_2$, SnF$_2$
Ge: GeCl$_2$, GeBr$_2$, GeI$_2$, GeF$_2$
Pb: PbCl$_2$, PbBr$_2$, PbI$_2$, PbF$_2$ Among these dihlides, desirable compounds are dihalides of tin and germanium, especially stannous chloride (SnCl$_2$) and germanous chloride (GeCl$_2$) being preferable.

Examples of olefins to be used in this invention include terminal olefins such as ethylene, propylene, 1-butene, isobutylene, 1-pentene, 1-hexene, 1-heptene, 1-octene, 1-nonene, 1-decene, 1,7-ontadiene, styrene, -methylstyrene etc., internal olefins such as 2-butene, 2-pentene, 2-methyl-2-butene, 2-hexene, 3-hexene, cyclohexene, cycloocta-1,5-diene etc., and conjugated dienes such as buta diene, isoprene, piperylene etc. Further, the process of this invention may also be applied to such ethylenically unsaturated compounds containing olefinic linkages such as vinyl acetate, acryl acetate, methacryl acetate, methyl acrylate, methyl methacrylate, 3,8-nonadienoic acid esters, e.g., methyl 3,8-nonadienoate, ethyl 3,8-nonadienoate, propyl 3,8-nonadienoate etc., allyl alcohol etc. Among these ethylenically unsaturated compounds, it is preferred to apply the process of this invention to olefins having a double bond at the terminal, especially lower olefins such as ethylene, propylene, and 1-butene, and particularly propylene.

The process of this invention is, as described above, a process for producing aldehydes which comprises reacting an olefin with carbon monoxide and hydrogen employing the platinum catalyst mixture described herein.

The molar ratio of the platinum (II) compound to the dihalide of Ge, Sn or Pb when the pre-synthesized platinum (II) compound is used, is 1:1-200, preferably 1:1-50,and the molar ratio of the platinum (0) compound, the organometallic compound of a Group IV-B metal, and the dihalide of Ge, Sn or Pb when a mixture or a reaction product or a complex compound obtained from the platinum (0) compound and the organometallic compound of a Group IV-B metal is used, is 1:1-10-:1-200, preferably 1:1-5:1-50.

The reaction temperature is 15°-150° C., preferably 60°-100° C., the reaction pressure is 0.1-30 MPa, preferably 3-10 MPa and the molar ratio of hydrogen to carbon monoxide is from 1:20 to 20:1, preferably from 1:10 to 10:1.

Further, a solvent which does not adversely affect the oxo reaction may be employed, examples thereof which include ketones such as acetone, methyl ethyl ketone, methyl isobutyl ketone, acetophenone and cyclohexanone, aromatic hydrocarbons such as benzene, toluene and xylene, halogenated aromatic hydrocarbons including o-dichlorobenzene, ethers such as tetrahydrofuran, dimethoxyethane and dioxane, halogenated paraffins including methylene chloride, paraffins such as isooctane, and other solvents such as acetonitrile.

The following Examples are regarded by us as being illustrative of the best mode of carring out the subject process and it is intended that they do not constitute limits on the scope or spirit of the instant invention.

EXAMPLES 1-4

Each run shown in Examples 1-4 was conducted according to a method involving the oxidative addition reaction of (PPh$_3$)$_2$Pt(CO)$_2$ and R$_3$SnCl or R$_3$SnH in the reaction system to produce the corresponding Pt (II)-Sn(IV) complex. The procedures of the experiments are as follows:

Into a stainless steel autoclave having an internal volume of 200 ml. and equipped with an electromagnetic stirrer were charged the predetermined amounts of (PPh$_3$)$_2$Pt(CO)$_2$,SnCl$_2$.2H$_2$O and R$_3$SnCl (R=n-Bu or Ph) or R$_3$SnH (R=n-Bu or Ph), to form (PPh$_3$)$_2$RPt-SnR$_2$Cl/SnCl$_2$ and 30 ml. of toluene as a solvent and, after displacing the inside of the autoclave with nitrogen gas, stirring was performed at room temperature for an hour. Thereafter, the predetermined amount, i.e., 2.5 g. of propylene was charged into the autoclave under pressure, which was then dipped in a constant temperature tank maintained at the predetermined temperature, and when the internal temperature of the autoclave reached the reaction temperature, a synthesis gas having a molar ratio of $H_2/CO$ of 1:1 was introduced and the reaction pressure was set at the predetermined pressure before starting stirring. After stirring for the predetermined period of time, the autoclve was rapidly cooled to terminate the reaction, and the gaseous and liquid products were analyzed by gas chromatography. The results are shown in Table I.

COMPARATIVE EXAMPLE 1

For comparison, the results obtained from the experiment using similar procedures to those in Example 2 except that stannic chloride was employed in place of the Sn (IV) organometallic compounds in Examples 1-4. As evident from the results, it can be seen that the process of this invention gave a higher percent formation of a linear aldehyde.

temperature, a synthesis gas having a molar ratio of $H_2/CO$ of 1:1 was introduced and the reaction pressure was set at the predetermined pressure before starting stirring. After stirring for the predetermined period of time, the autoclave was rapidly cooled to terminate the reaction, and the gaseous and liquid products were analyzed by gas chromatography. The results are shown in Table II.

COMPARATIVE EXAMPLES 2-4

For comparison, the results obtained from the experiments carried out using similar procedures to those in Example 5 except that $(Ph_3P)_2ClPt-SnCl_3$ or $(Ph_3P)_2PtCl_2$ was employed in place of the complex compounds of this invention are shown in Table II. As evident from the results, it can be seen that the process of this invention gave a higher percent formation of a linear aldehyde.

TABLE I

| Exp. No. | Pt. Compd. (0.2 mmol) | Sn Compd. (0.3 mmol) | $SnCl_2 \cdot 2H_2O$ (mmol) | Reaction Temp. (°C.) | Reaction* Pressure ($kg/cm^2$) | Reaction Period (hr.) | Percent Conv. of Propylene (mol %) | Yield of Butyl Aldehyde (mol %) | Linear/ Branched Ratio | Yield of Propane (mole %) |
|---|---|---|---|---|---|---|---|---|---|---|
| 1 | $(Ph_3P)_2Pt(CO)_2$ | $n-Bu_3SnH$ | 1.0 | 90 | 60 | 4 | 85.1 | 81.5 | 16.2 | 3.3 |
| 2 | $(Ph_3P)_2Pt(CO)_2$ | $Ph_3SnH$ | 1.0 | 80 | 60 | 4 | 16.7 | 14.4 | 28.1 | 2.2 |
| 3 | $(Ph_3P)_2Pt(CO)_2$ | $n-Bu_3SnCl$ | 1.0 | 80 | 60 | 4 | 72.6 | 68.3 | 12.0 | 4.0 |
| 4 | $(Ph_3P)_2Pt(CO)_2$ | $Ph_3SnCl$ | 1.0 | 80 | 60 | 4 | 39.8 | 36.0 | 15.5 | 3.6 |
| Comparative Ex. 1 | $(Ph_3P)_2Pt(CO)_2$ | $SnCl_4$ | 1.0 | 80 | 60 | 4 | 64.4 | 60.4 | 5.9 | 3.7 |

Conditions: Propylene 60 mmol, toluene (solvent) 30 ml, and $H_2/CO = 1/1$
*The initial pressure at the start of the reaction.

TABLE II

| Exp. No. | Pt Compound (0.2 mmol) | $SnCl_2 \cdot 2H_2O$ (mmol) | Reaction Temp. (°C.) | Reaction* Pressure ($kg/cm^2$) | Reaction Period (hr.) | Percent Conversion of Propylene (mol %) | Yield of Butyl Aldehyde (mol %) | Linear/ Branched Ratio | Yield of Propane (mol %) |
|---|---|---|---|---|---|---|---|---|---|
| Ex. 5 | $(Ph_3P)_2PhPt-SnClPh_2$ | 1.0 | 80 | 60 | 4 | 61.2 | 58.4 | 16.0 | 2.6 |
| 6 | $(Ph_3P)_2PhPt-SnClPh_2$ | 1.0 | 80 | 60 | 9 | 98.3 | 94.8 | 15.8 | 3.2 |
| 7 | $(Ph_3P)_2PhPt-SnClPh_2$ | 0.2 | 80 | 60 | 4 | 20.4 | 17.9 | 22.5 | 2.4 |
| 8 | $(Ph_3P)_2PhPt-SnClPh_2$ | 2.0 | 80 | 60 | 4 | 64.8 | 60.8 | 14.3 | 3.8 |
| 9 | $(Ph_3P)_2PhPt-SnClPh_2$ | 1.0 | 80 | 30 | 4 | 36.4 | 33.6 | 13.8 | 2.6 |
| 10 | $(Ph_3P)_2PhPt-SnClPh_2$ | 1.0 | 100 | 60 | 4 | 94.0 | 85.1 | 10.5 | 8.6 |
| 11 | $(Ph_3P)_2PhPt-SnPh_3$ | 1.0 | 80 | 60 | 4 | 56.3 | 51.5 | 24.9 | 4.6 |
| Comparative Ex. 2 | $(Ph_3P)_2ClPt-SnCl_3$ | 1.0 | 80 | 60 | 4 | 76.1 | 70.9 | 5.7 | 4.9 |
| 3 | $(Ph_3P)_2PtCl_2$ | 1.0 | 80 | 60 | 4 | 70.4 | 64.8 | 5.5 | 5.4 |
| 4 | $(Ph_3P)_2PtCl_2$ | 1.0 | 80 | 60 | 1 | 19.9 | 17.2 | 5.5 | 2.6 |

Conditions: Propylene 60 mmol, toluene (solvent) 30 ml, and $H_2/CO = 1/1$
*The initial pressure at the start of the reaction

EXAMPLES 5-11

Each experiment shown in Examples 5-11 illustrates an example where a complex compound is pre-synthesized from a plastinum (0) compound and a tin organometallic compound.

The experiments shown in Experiments 5-11 were conducted according to the following procedures.

Into a stainless steel autoclave having an internal volume of 200 ml. and equipped with an electromagnetic stirrer were charged the predetermined amounts of the complex compound of this invention and $SnCl_2 \cdot 2H_2O$ and 30 ml. of toluene as a solvent and, after displacing the inside of the autoclave with nitrogen gas, the predetermined amount, i.e., 2.5 g. of propylene was charged into the autoclave under pressure. This was then dipped in a constant temperature tank maintained at the predetermined temperature, and when the internal temperature of the autoclave reached the reaction

EXAMPLE 12

To a stainless steel autoclave having an internal volume of 200 ml. and equipped with an electromagnetic stirrer was added 30 ml. of toluene as a solvent followed by $(PPh_3)_2PhPt-Sn(Ph)_2Cl$ (0.2 mmol) synthesized according to the procedures of Example 5 and $SnCl_2 \cdot 2H_2O$ (1 mmol). After displacing the inside of the autoclave by nitrogen gas, 5.0 g. (60 mmol) of hexene was added. This autoclave was placed in a constant temperature tank maintained at 80° C. When the internal temperature of the autoclave reached 80° C., a synthesis gas having a molar ratio of $H_2/CO$ of 1:1 was introduced and the reaction was carried out while maintaining the pressure at 50 $kg/cm^2$ for 2 hours. Thereafter, the autoclave was rapidly cooled, the gaseous and liquid products were taken out and analyzed by gas chromatography. The results are shown in Table III.

COMPARATIVE EXAMPLE 5

For comparison, the results of the oxo process of hexene-1 carried out using similar procedures to those in Example 12 except that (PPh$_3$)$_2$ClPt-SnCl$_2$ was employed in place of the platinum (II) compound employed in Example 12 are shown in Table III. As evident from Table III, it can be seen that the process of this invention provides a high selectivity for formation of a linear aldehyde.

TABLE III

| Exp. No. | Pt Compound (0.2 mmol) | SnCl$_2$·2H$_2$O (mmol) | Reaction Temp. (°C.) | Reaction* Pressure (kg/cm$^2$) | Reaction Period (hr) | Percent Conversion of Hexene (mol %) | Yield of Heptyl Aldehyde (mol %) | Linear/ Branched Ratio | Yield of Hexene-2,3 (mol %) |
|---|---|---|---|---|---|---|---|---|---|
| Ex. 12 | (PPh$_3$)$_2$PhPt—SnClPh$_2$ | 1.0 | 80 | 50 | 2 | 58.3 | 47.9 | 30.9 | 6.6 |
| Comparative Ex. 5 | PtCl(PPh$_3$)$_2$·SnCl$_3$ | 1.0 | 80 | 50 | 2 | 72.9 | 57.8 | 8.5 | 9.7 |

Conditions: Hexene-1 60 mmol, toluene (solvent) 30 ml, and H$_2$/CO = 1/1

What is claimed is:

1. A process for producing aldehydes which comprises reacting an olefin with a mixture of hydrogen and carbon monoxide, in a molar ratio of about 1:20 to 20:1, at a temperature of about 15°–150° C., and a pressure of about 0.1–30 MPa, in the presence of a catalyst mixture comprising:
(a) a platinum (II) organometallic compound of the following general formula:

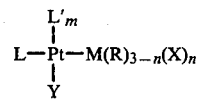

wherein M represents Si, Ge, Sn or Pb; L represents an unidentate or bidentate ligand containing P, As or Sb; L' represents a coordination compound; Y represents an alkyl group, an aryl group, an alkoxy group, an aryloxy group, or hydrogen; R independently represents an alkyl group, an aryl group, an alkoxy group or an aryloxy group; X independently represents halogen or hydrogen, n represents an integer of 0, 1 or 2; and m is 1 when L is an unidentate ligand or 0 when L is a bidentate ligand; and
(b) a dihalide of Ge, Sn or Pb.

2. The process of claim 1 wherein said platinum (II) compound is selected from:
(PPh$_3$)$_2$(Ph)Pt-Sn(Ph)$_2$Cl,
(PPh$_3$)$_2$(Ph)Pt-Sn(Ph)$_3$,
(PPh$_3$)$_2$(Ph)Pt-Sn(CH$_3$)(Ph)Cl,
(PPh$_3$)$_2$(Ph)Pt-Sn(CH$_3$)$_2$Cl
(PPH$_3$)$_2$(CH$_3$)Pt-Sn(CH$_3$)$_2$Cl
(PPh$_3$)$_2$(CH$_3$-C$_6$H$_4$)Pt-Sn(CH$_3$-C$_6$H$_4$)$_2$Cl,
(PPh$_3$)$_2$(Ph)Pt-Sn(Ph)$_2$Br, and
(PPh$_3$)$_2$(Ph)Pt-Sn(Ph)$_2$I.

3. The process of claim 1 wherein said dihalide is SnCl$_2$ or GeCl$_2$.

4. The process of claim 1 in which said platinum (II) compound is a reaction product obtained from:
(a) a platinum (0) compound of the following general forula:

Pt(L)(L')$_{n'}$ wherein L represents an unidentate or bidentate ligand containing P, As or Sb, L' independently represents a coordination compound, and n' represents an integer of 1, 2 or 3; and
(b) a Group IV-A organometallic compound of the following general formula:

YM(R)$_{3-n}$(X)$_n$ wherein M represents Si, Ge, Sn or Pb; Y represents an alkyl group, an aryl group, an alkoxy group, an aryloxy group or hydrogen; R independently represents an alkyl group, an aryl group, an alkoxy group or an aryloxy group; X independently represents halogen or hydrogen; and n represents an integer of 0, 1 or 2.

5. The process of claim 4 wherein said platinum (0) compound is selected from:
Pt(PPh$_3$)$_4$,
Pt(PPh$_3$)$_3$,
Pt(CO)$_2$(PPh$_3$)$_2$,
Pt(CO)PPh$_3$)$_3$,
Pt(CH$_2$=CH$_2$)(PPh$_3$)$_2$,
Pt(PhC|CPh((PPh$_3$)$_2$, and

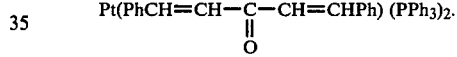

6. The process of claim 4 wherein said Group IV-A organometallic compound is selected from Sn(Ph)$_4$; Sn(n-C$_4$H$_9$)$_4$; Sn(CH$_3$)$_4$; Sn(Ph)$_3$Cl; Sn(C$_2$H$_5$)$_3$Cl; Sn(CH$_3$)$_3$Cl; Sn(PhCH$_2$-)$_2$Cl$_2$; Sn(CH$_3$)$_2$Cl$_2$; Sn(n-C$_4$H$_9$)$_2$I$_2$; Sn(n-C$_4$H$_9$)Cl$_3$; Sn(Ph)$_3$H; Sn(n-C$_4$H$_9$)$_3$H; Sn(C$_2$H$_5$)$_3$H; Sn(n-C$_4$H$_9$)$_2$H$_2$; Sn(n-C$_4$H$_9$)H$_3$; Ge(Ph)$_4$; and Ge(Ph)$_3$Cl.

7. The process of claim 1 wherein the molar ratio of said platinum (II) compound to said dihalide is about 1:1-200.

8. The process of claim 4 wherein the molar ratio of platinum (0) compound:Group IV-A organometallic compound:dihalide of Ge, Sn or Ph is about 1:1-10-:1-200.

9. The process of claim 1 wherein said olefin is propylene.

10. The process of claim 1 further comprising an inert reaction solvent.

11. A process for producing n-butyraldehyde which comprises reacting propylene in an inert solvent with a mixture of hydrogen and carbon monoxide, in a molar ratio of about 1:10 to 10:1, at a temperature of about 60°–100° C., and a pressure of about 3–10 MPa, in the presence of a catalyst mixture comprising:
(a) a platinum (II) organometallic compound selected from: (Ph$_3$P)$_2$PhPt-SnClPh$_2$, (Ph$_3$P)$_2$PhPt-SnPh$_3$, (Ph$_3$P)$_2$-n-BuPt-SnHn-Bu$_2$, (Ph$_3$P)$_2$PhPt-SnPh$_2$H, (Ph$_3$P)$_2$n-BuPt-SnCln-Bu$_2$, (Ph$_3$P)$_2$PhPt-SnPh$_2$Cl; and
(b) SnCl$_2$, wherein the molar ratio of platinum (II) compound: SnCl$_2$ is about 1:1-50.

* * * * *